US010557837B2

United States Patent
Kageyama et al.

(10) Patent No.: US 10,557,837 B2
(45) Date of Patent: Feb. 11, 2020

(54) MASS-SPECTROMETRY-DATA PROCESSING SYSTEM

(71) Applicant: SHIMADZU CORPORATION, Kyoto-shi, Kyoto (JP)

(72) Inventors: Tetsuya Kageyama, Ibaraki (JP); Yoshikatsu Umemura, Osaka (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/322,778

(22) PCT Filed: Jan. 13, 2015

(86) PCT No.: PCT/JP2015/050622
§ 371 (c)(1),
(2) Date: Dec. 29, 2016

(87) PCT Pub. No.: WO2016/002233
PCT Pub. Date: Jan. 7, 2016

(65) Prior Publication Data
US 2017/0131248 A1    May 11, 2017

(30) Foreign Application Priority Data
Jul. 3, 2014  (WO) .................. PCT/JP2014/067813

(51) Int. Cl.
*G01N 30/86*     (2006.01)
*G01N 30/72*     (2006.01)
(Continued)

(52) U.S. Cl.
CPC ......... *G01N 30/8675* (2013.01); *G01N 27/62* (2013.01); *G01N 30/7233* (2013.01);
(Continued)

(58) Field of Classification Search
CPC .................................................. G01N 30/8675
See application file for complete search history.

(56) References Cited

U.S. PATENT DOCUMENTS

2001/0007349 A1    7/2001  Nagai
2005/0063864 A1*   3/2005  Sano .................. G01N 33/6848
                                                          422/68.1
(Continued)

FOREIGN PATENT DOCUMENTS

JP   2001-249114 A    9/2001
JP   2005-083952 A    3/2005

OTHER PUBLICATIONS

Written Opinion for PCT/JP2015/050622 dated Mar. 10, 2015. [PCT/ISA/237].
(Continued)

*Primary Examiner* — Manuel L Barbee
*Assistant Examiner* — Raymond L Nimox
(74) *Attorney, Agent, or Firm* — Sughrue Mion, PLLC

(57) ABSTRACT

Nonuse-indication information can be set for each peak on a mass spectrum collected in a compound database, as attribute information, the nonuse-indication information allowing the selection of whether to be used in a database search. For example, nonuse-indication information is set in advance to a noise peak mixed in actual measurement, an impurity-originated peak, and the like. In identifying a compound, when nonuse-indication information is read from the database for a database search together with a mass spectrum, an unnecessary information deleting section transmits a mass spectrum from which a peak set with the nonuse-indication information is deleted, to a compound candidate extracting section and a scoring section. Therefore, a peak set with the nonuse-indication information is ignored in, for example, calculating the score of a compound
(Continued)

candidate, which allows a score with a high accuracy to be calculated, resulting in an improved identification accuracy.

7 Claims, 4 Drawing Sheets

(51) Int. Cl.
  *H01J 49/00* (2006.01)
  *G01N 30/02* (2006.01)
  *G01N 27/62* (2006.01)
  *G16C 20/20* (2019.01)
  *H01J 49/26* (2006.01)
(52) U.S. Cl.
  CPC ............ *G16C 20/20* (2019.02); *H01J 49/004* (2013.01); *H01J 49/26* (2013.01); *G01N 2030/027* (2013.01)

(56) References Cited

U.S. PATENT DOCUMENTS

| | | | | |
|---|---|---|---|---|
| 2006/0169889 A1* | 8/2006 | Yokosuka | ........... | H01J 49/0031 250/288 |
| 2008/0300795 A1* | 12/2008 | Sadygov | ............ | G01N 33/6848 702/19 |
| 2013/0131998 A1* | 5/2013 | Wright | ................... | G16C 20/20 702/27 |
| 2013/0206979 A1* | 8/2013 | Bonner | ............... | H01J 49/0031 250/282 |
| 2013/0306857 A1* | 11/2013 | Yamaguchi | ........... | H01J 49/004 250/282 |
| 2014/0012515 A1* | 1/2014 | Taneda | ................... | G06F 19/708 702/32 |
| 2014/0045273 A1* | 2/2014 | Cerda | .................... | G01N 27/62 436/173 |
| 2014/0142865 A1* | 5/2014 | Wright | ................ | H01J 49/0036 702/23 |
| 2014/0274751 A1* | 9/2014 | Sadowski | .......... | G01N 30/8668 506/8 |

OTHER PUBLICATIONS

International Search Report for PCT/JP2015/050622 dated Mar. 10, 2015.

Communication dated Nov. 20, 2018, from State Intellectual Property Office of the P.R.C. in counterpart application No. 201580035341.5.

* cited by examiner

⇒ USED IN COMPOUND CANDIDATE EXTRACTION

⇒ USED IN SCORING

MASS-SPECTROMETRY-DATA PROCESSING SYSTEM

CROSS REFERENCE TO RELATED APPLICATIONS

This application is a National Stage of International Application No. PCT/JP2015/050622 filed Jan. 13, 2015, claiming priority based on International Application No. PCT/JP2014/067813 filed Jul. 3, 2014, the contents of all of which are incorporated herein by reference in their entirety.

TECHNICAL FIELD

The present invention relates to a data-processing system that analyzes data collected with a mass spectrometer, more specifically, relates to a data-processing system that identifies an unknown compound in a sample or estimates the structure of the unknown compound, using a database in which mass spectra corresponding to a large number of known compounds are collected.

BACKGROUND ART

Methods for identifying an unknown compound in a sample using a gas chromatograph mass spectrometer (GC-MS) or a liquid chromatograph mass spectrometer (LC-MS) include a well-known method involving a database search using a database (may be called a library) in which mass spectra (including $MS^n$ spectra, where n is an integer of two or more) corresponding to a large number of known compounds are collected. Databases in which such mass spectra are collected range from general-purpose databases being exhaustive collection of the mass spectra of general compounds, such as the NIST database compiled by the National Institute of Standards and Technology (NIST) (US), and the Wiley database compiled by John Wiley & Sons, Inc., a publisher, to specified databases of compounds in specific fields or compounds for specific purposes, such as databases for agricultural chemical, medicine, and metabolite (see Patent Literature 1, etc.).

Such databases of mass spectra are created in general based on data obtained by actually measuring standard preparations of target compounds using a measurement machine. Usually, in collecting data, a mass spectrum includes unnecessary elements such as noise due to various factors. For example, in an LC-MS, ions originating from impurities included in a mobile phase used in an LC may appear on a mass spectrum in the form of the unnecessary elements. In addition, ions originating from impurities separated out from a column may also appear on a mass spectrum in the form of unnecessary elements. As described above, it is possible that unnecessary elements are included in a mass spectrum, but it is not desirable in terms of the reliability of analysis to edit the obtained mass spectrum before storing it to a database. Therefore, even when including unnecessary elements, such a mass spectrum is usually collected in a database as it is.

While there are a variety of algorithms for searching database based on mass spectra, algorithms commonly include two steps: extracting, from a database, a plurality of compounds the mass spectra of which have similar spectral patterns to that of an unknown compound to some extent, as compound candidates; and then calculating scores of strict degrees of match of the compound candidates in spectral pattern so that the compound candidates are presented to a user in a descending order of the scores. In performing such data processing, unnecessary elements included in a mass spectrum in the database can lead to the presentation of a false positive or a false negative, which may decrease the accuracy of a search.

On mass spectra of similar compounds having a common main skeleton, a common spectral pattern originating from the common main skeleton appears, which makes the mass spectra significantly similar to one another. In the case of a database in which a large number of such similar compounds are collected, for an unknown compound being one of such similar compounds, a large number of compounds similar to one another in mass spectrum are extracted as compound candidates. The spectral patterns of mass spectra of a plurality of compound candidates extracted in such a manner share a lot of common portions, and thus calculated scores hardly yield significant differences from one another, which makes it difficult to assess which of the compound candidates is a correct compound even when the scores are compared. In addition, this reduces the possibility that the correct compound is highly ranked. Furthermore, in identifying a compound using mass spectra, an analysis operator often determines the final result by visually confirming the match of a mass spectrum, but if the number of extracted compound candidates is too large, the visual confirmation operation poses a heavy workload on the operator and an operation error such as overlooking easily occurs.

CITATION LIST

Patent Literature

[Patent Literature 1] JP 2005-83952 A

SUMMARY OF INVENTION

Technical Problem

The present invention has been developed to solve the previously-described problem. Its objective is to provide a mass spectrometry data-processing system capable of improving the accuracy of identifying a compound or estimating a structure by searching a database even when an unnecessary element such as noise is included in a mass spectrum collected in a database.

Another objective of the present invention is to provide a mass spectrometry data-processing system capable of, even when a large number of similar compounds having a common main skeleton are collected in a database and one of the compounds is a target compound, eliminating the influence of similar compounds in a database search, so as to identify a target compound with exactitude.

Solution to Problem

A first specific form of the present invention developed for solving the previously-described problem is a mass spectrometry data-processing system that estimates the substance or the structure of an unknown compound by checking a mass spectrum obtained by subjecting the unknown compound to mass spectrometry against a database in which the mass spectra of known compounds are collected, the mass spectrometry data-processing system including:

a) a database in which mass spectra of known compounds are collected, and nonuse-indication information indicating that it is not used in a step in a later-described database search can be set as attribute information in association with at least some of ion peaks appearing on a mass spectrum; and b) a search processing section for performing a database search on a mass spectrum obtained for the unknown compound using the database through the use of a mass spectrum from which an ion peak with the nonuse-indication information attached in the attribute information is excluded when performing the database search.

The term "mass spectrometry" used herein includes MS/MS analysis including fragmentation operation on ions and MS$^n$ analysis, where n is three or more, and the term "mass spectrum" used herein includes an MS/MS spectrum and an MS$^n$ spectrum.

In the mass spectrometry data-processing system according to the first specific form of the present invention, the mass spectra collected in the database are normally line spectra having been subjected to centroid processing. For example, in an ion source employing electron ionization, a molecular ion is easily fragmented to generate various fragment ions in ionization, and thus a peak originating from a molecular ion as well as various fragment ion peaks appear on amass spectrum. In addition, since many elements have natural isotopes, a molecular ion peak or a fragment ion peak is accompanied with a monoisotopic mass peak as well as one or more isotope peaks. That is, on a mass spectrum, ion peaks appear at a plurality of different positions on the mass-to-charge ratio m/z axis. The database in the mass spectrometry data-processing system according to the first specific form of the present invention is configured to allow, for example, nonuse-indication information to be set for each ion peak, in other words, for each mass-to-charge ratio on a mass spectrum, as attribute information.

Nonuse-indication information may be set when e mass spectrum is collected in the database or may be set after the mass spectrum is collected in the database. In addition, nonuse-indication information may be newly set to a mass spectrum having been already collected in the database, or nonuse-indication information having been set to a mass spectrum may be changed. In this case, security measures are desirably taken so that the nonuse-indication information will not be changed due to an error or intentionally, For example, at the time of collecting, in a database, a mass spectrum obtained by performing actual measurement on a known compound, when there is an ion peak clearly estimated that the ion peak should not be generated from the compound, that is, clearly estimated to be noise, setting nonuse-indication information to the ion peak may suffice.

When an unknown compound in a sample is to be identified, and a mass spectrum obtained by subjecting the unknown compound to mass spectrometry is given, the search processing section performs a database search on the mass spectrum. At this point, attribute information is checked for each mass spectrum collected in the database, and when there is an ion peak attached with nonuse-indication information on a mass spectrum, the mass spectrum from which the ion peak is excluded is to be subjected to a comparison with the mass spectrum of the unknown compound. With this configuration, as previously described, when a noise peak is attached with nonuse-indication information, the noise peak is not involved in the comparison of spectral patterns or the like, which avoids a decrease in the accuracy of searches due to the presence of a noise peak.

As a preferable specific form of embodiment of the mass spectrometry data-processing system according to the present invention, the search processing section preferably includes: a candidate extracting section for comparing the patterns of mass spectra to extract a plurality of compounds to be candidates; and a ranking section for ranking the plurality of extracted candidate compounds based on the similarities of mass spectra, the nonuse-indication information preferably includes: first nonuse-indication information indicating not being used in both of extracting the compounds by the candidate extracting section and ranking the compound candidates by the ranking section; and second nonuse-indication information indicating not being used only in ranking the compound candidates by the ranking section, and the candidate extracting section preferably extracts a plurality of compound candidates using mass spectra from which an ion peak attached with the first nonuse-indication information is excluded, and the ranking section preferably ranks compound candidates using mass spectrum from which an ion peak attached with at least one of the first nonuse-indication information and the second nonuse-indication information is excluded.

In this configuration, the processing of a database search performed by the search processing section includes two steps: a step of extracting a plurality of compound candidates by the comparison of spectral patterns; and a step of calculating scores indicating the similarities of the compound candidates, and ranking the compound candidates, for example, in accordance with the scores. To distinguish an ion peak not to be used in both steps and an ion peak to be used in the step of extracting the compound candidates but not to be used in the step of ranking, two kinds of nonuse-indication information are assigned. Therefore, in the database search process by the search processing section, any specific ion peak appearing on a mass spectrum in a database can be ignored, or a database search can be performed in such a manner that a specific ion peak appearing on a mass spectrum in the database is taken into account in the step of extracting the plurality of compound candidate, whereas the same ion peak is ignored in the step of ranking.

For example, in the case where a large number of similar compounds having a common main skeleton are present in a database, and one of such compounds is a target compound being an identification object, an ion peak corresponding to the main skeleton may be attached with second nonuse-indication information. In this case, in the step of extracting a plurality of compound candidates, the ion peak corresponding to the main skeleton is taken into account, and thus a large number of similar compounds having the same main skeleton as the main skeleton of the target compound are extracted as the compound candidates. Meanwhile, when the score of each of the compound candidate extracted in such a manner is calculated, an ion peak corresponding to the same main skeleton is ignored, and thus the similarity and the dissimilarity of an ion peak characteristic of each compound other than the main skeleton is significantly reflected in the score.

As a result, even when a large number of similar compounds are present, a correct compound out of the similar compounds is likely to be given a high score, which allows the correct compound to be obtained as an identification result accurately. In addition, compound candidates can be narrowed accurately in the step of ranking, which can reduce a workload on the operator when the operator performs the visual confirmation of a match of a mass spectrum. Furthermore, the occurrence of a confirmation error or the like by the operator can be reduced.

A second specific form of the present invention developed for solving the previously described problem is a mass spectrometry data-processing system that estimates an unknown compound with a database search using a database in which mass spectra of known compounds are collected, the mass spectrometry data-processing system including:

a) a database in which mass spectra are collected, and priority indication information indicating that it is used preferentially in a database search can be set as attribute information in association with at least some of ion peaks appearing on a mass spectrum; and b) a search processing section for performing a database search by comparing a mass spectrum of an unknown compound with mass spectra in the database to extract compound candidates that is supposed to be an unknown compound of interest, the search processing section extracting the compound candidates on one of the conditions that an ion peak set with the priority indication information is present on the mass spectrum of the unknown compound, or creating a search result that allows, of compound candidates extracted through a database search not using the priority indication information, a compound candidate of which an ion peak set with the priority indication information is present on the mass spectrum of the unknown compound to be distinguished from the other compound candidates.

In the mass spectrometry data-processing system according to the second specific form of the present invention, as with the nonuse-indication information in the first specific form, for example, priority indication information can be set for each ion peak, that is, for each mass-to-charge ratio on a mass spectrum, as one of the kinds of attribute information.

When an unknown compound in a sample is to be identified, and a mass spectrum obtained by subjecting the unknown compound to mass spectrometry is given, the search processing section performs, for example, a normal database search on the mass spectrum to extract a plurality of compound candidates having high similarities in spectral pattern. Subsequently, the search processing section performs the confirmation of whether or not there is any ion peak set with priority indication information on mass spectra corresponding to the plurality of extracted compound candidates, and excludes a compound candidate of which the ion peak set with priority indication information is absent on the mass spectrum of the unknown compound. Alternatively, instead of excluding, the search processing section creates and displays a search result so that, of the plurality of compound candidate extracted through the database search, a compound candidate of which an ion peak set with priority indication information is present on the mass spectrum of the unknown compound can be distinguished from the other compound candidates.

Therefore, in the case where there are a large number of similar but different compounds having a common main skeleton, setting priority indication information to not an ion peak corresponding to such a main skeleton but to other ion peaks characteristic of partial structures of individual compounds allows compound candidates having a partial structure present in an unknown compound, that is, being highly likely to be correct, to be included in final compound candidates or to be presented to the operator so as to be distinguished from the other compound candidates.

In the mass spectrometry data-processing system according to the second specific form of the present invention, more preferably, the database may be configured to allow threshold information to be set, as attribute information, to an ion peak set with the priority indication information, in addition to the priority indication information, the threshold information being used for assessing the intensity ratio of the signal intensity of the ion peak to the signal intensity of a specific peak on a mass spectrum in which the ion peak is present.

Here, the "specific peak" may be set to a peak at a specific mass-to-charge ratio on a mass spectrum, or may be set to a peak showing a maximum intensity irrespective of the mass-to-charge ratio.

Then, in this configuration, the search processing section may be configured to extract compound candidates on one of the conditions that an ion peak set with the priority indication information is present on the mass spectrum of the unknown compound, and, on the mass spectrum of the unknown compound, the intensity ratio of the signal intensity of the ion peak to the signal intensity of the specific peak is equal to or greater than the threshold information set to the ion peak together with the priority indication information.

With this configuration, even when an ion peak set with priority indication information is observed on the mass spectrum of the unknown compound, a compound candidate including an ion peak the signal intensity of which is assumed to be insignificant is substantially excluded from the candidates of the unknown compound. This allows the compound candidates to be accurately narrowed, which in turn allows the operator to specify a correct compound easily.

Advantageous Effects of Invention

With the mass spectrometry data-processing system according to the first and second specific forms of the present invention, it is possible to improve, while using mass spectra obtained through actual measurement in a database, the accuracy of the identification and the structure analysis of a compound through a database search using this database.

DESCRIPTION OF EMBODIMENTS

Figure 1:
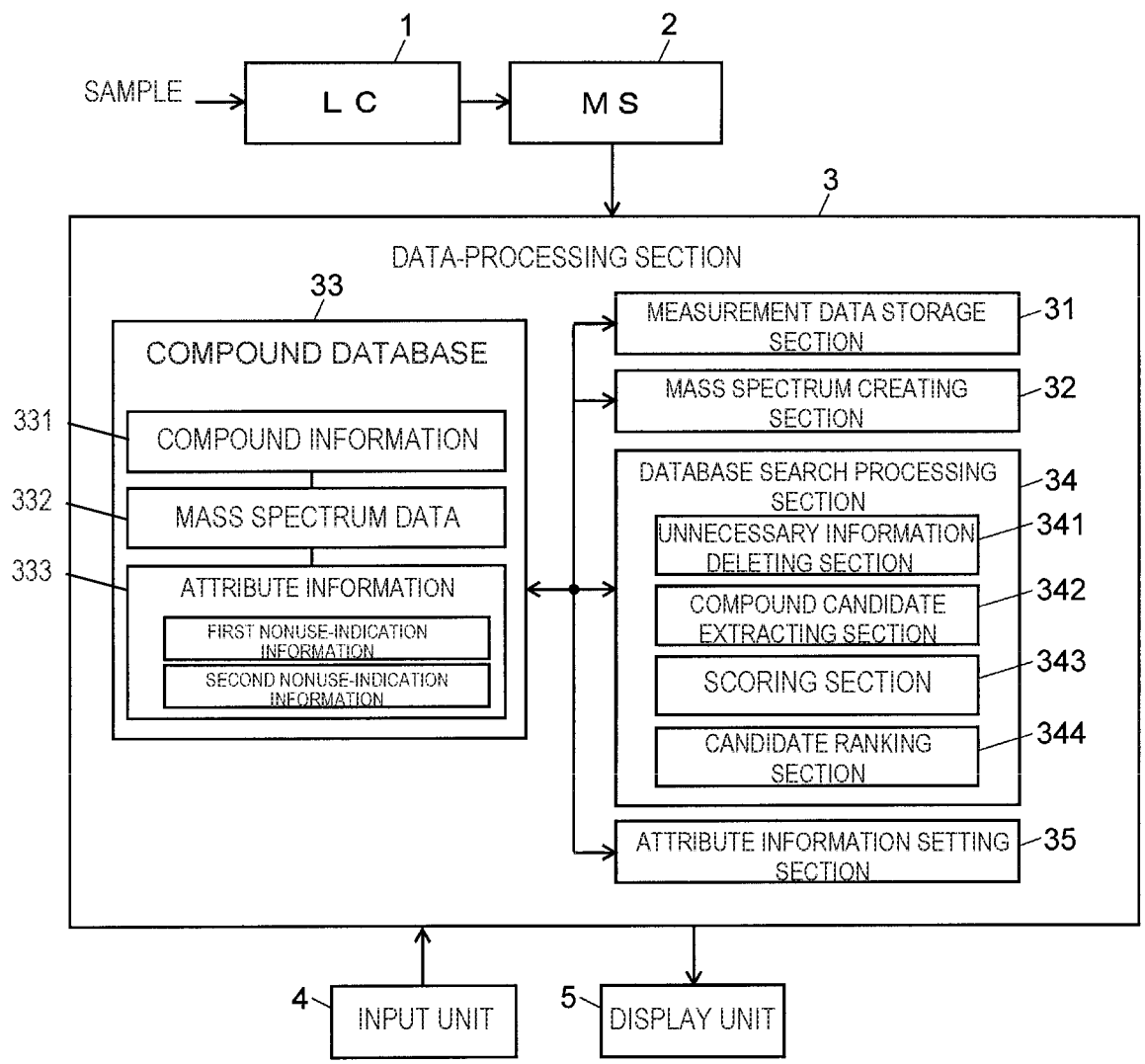
FIG. 1 is a schematic configuration diagram of a first embodiment of an LC-MS system including a mass spectrometry data-processing system according to the present invention.
Figure 2A:
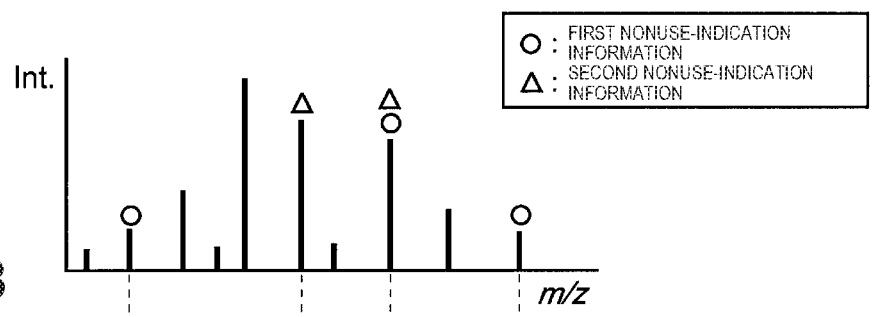
FIG. 2A, FIG. 2B, and FIG. 2C are diagrams illustrating examples of a compound identification process in the LC-MS system in the first embodiment.
Figure 2B:
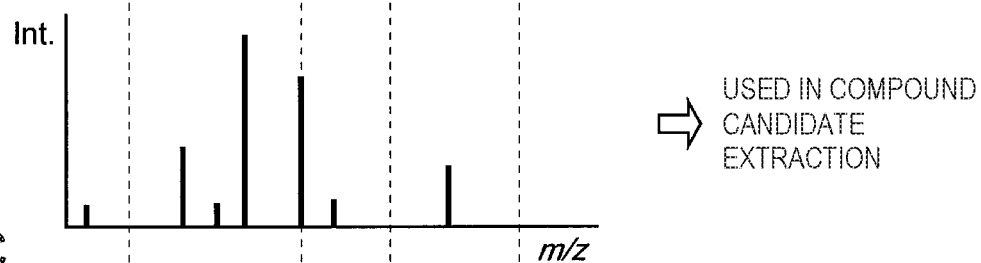
Figure 2C:
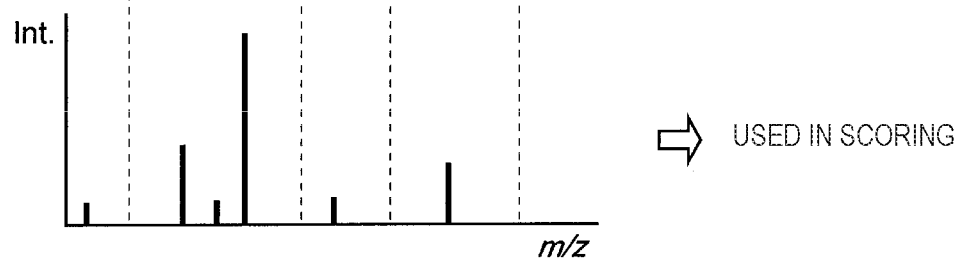

A first embodiment of an LC-MS system using a mass spectrometry data-processing system according to the present invention is described with reference to the attached drawings. FIG. 1 is a schematic configuration diagram of the LC-MS system of the present embodiment, and FIG. 2A, FIG. 2B, and FIG. 2C are diagrams illustrating examples of a compound identification process in the LC-MS system in the present embodiment.

The LC-MS system in the present embodiment includes a liquid chromatograph (LC) 1, a mass spectrometry section (MS) 2, and a data-processing section 3.

Although not being illustrated, the liquid chromatograph 1 includes, as basic components for a liquid chromatograph, a mobile phase container in which a mobile phase is stored, a pump for supplying the mobile phase at a certain flow velocity, an injector for injecting a liquid sample in a predetermined amount into the supplied mobile phase, a column for separating compounds contained in the liquid sample, and the like. The liquid chromatograph 1 transports the sample containing temporally separated compounds to the mass spectrometry section 2.

Although not being illustrated as with the liquid chromatograph 1, the mass spectrometry section 2 includes an atmospheric pressure ion source for ionizing compounds in a sample, an ion guide for transporting generated ions, a quadrupole mass filter for separating the ions in proportion to their mass-to-charge ratios m/z, an ion detector for detecting the separated ions, and the like. By repeating scan measurement over a predetermined mass-to-charge-ratio range using the quadrupole mass filter, the mass spectrometry section 2 can repeatedly collect mass spectrum data within the mass-to-charge-ratio range.

The data-processing section 3 includes, as functional blocks, a measurement data storage section 31, a mass spectrum creating section 32, a compound database 33, a database search processing section 34, and an attribute information setting section 35, and the database search processing section 34 includes an unnecessary information deleting section 341, a compound candidate extracting section 342, a scoring section 343, and ranking section 344. To the data-processing section 3, an input unit 4 operated by an analysis operator for setting a searching condition a database search and a display unit 5 for displaying the searching condition, a search result, and the like are connected.

Part or most of the functions of the data-processing section 3 can be implemented by executing predetermined data processing programs on a personal computer.

In the compound database 33, mass spectrum data 332 on a large number of compounds is registered being associated with compound information 331 containing a compound name, a structural formula, a molecular weight, and the like. This is the same as conventional systems. Here, attribute information 333 on the mass spectrum data 332 can be further registered. The attribute information is the following information.

For example, in a mass spectrum as illustrated in FIG. 2A, of which the horizontal axis represents a mass-to-charge ratio m/z, and the vertical axis represents a signal intensity, a plurality of peaks normally appear, including a peak originating from an intended target compound, peaks originating from impurities extraneous to a target compound, and noise peaks due to various factors other than the above. Such impurity-originated peak and noise peaks are desired to be absent on a mass spectrum, but such undesired peaks inevitably appear on a mass spectrum obtained through actual measurement. Therefore, when a database is created based on measured results, a mass spectrum including such undesired peaks will be registered.

In addition, a mass spectrum obtained through actual measurement includes a peak that can be an obstacle to identify the compound, while originating from a target compound. For example, in the case where a target compound is one of similar compounds having substantially the same main skeleton but differing in partial structure from one another, an ion peak originating from the main skeleton with a high signal intensity appears on a mass spectrum. However, the similar compounds cause such an ion peak to appear in common, which is not only useless to identify the target compound but also will trivialize the influence of a peak originating from a partial structure specific to the compound.

Thus, the LC-MS system in the present embodiment is configured to add, for each peak appearing on a mass spectrum, nonuse-indication information indicating that the peak is not used in database searches, that is, the peak is ignored, so as to prevent such peaks being unnecessary for identification or rather acting as an obstacle for identification from affecting a search result. Here, this nonuse-indication information is divided into two kinds: first nonuse-indication information and second nonuse-indication information, which will be described later.

The nonuse-indication information can be set by a user as appropriate for mass spectrum data 332 on any compound having already been registered in the compound database 33, or for mass spectrum data 332 on any compound to be newly registered in the compound database 33. For example, when the user performs a predetermined operation using the input unit 4, the attribute information setting section 35 displays a mass spectrum of a compound specified by the user on a screen of the display unit 5. When the user specifies on the displayed mass spectrum a peak not to be used for identification by a clicking operation or the like using the input unit 4, the attribute information setting section 35 recognizes the mass-to-charge ratio of the specified peak and writes information thereon as nonuse-indication information into predetermined storage area where attribute information 333 is stored in the compound database 33.

Of course, if the nonuse-indication information set in such a manner is rewritten due to an operation error or out of spite, the reliability of analysis will be decreased, thus security measures are desirably taken so that a new setting or change of nonuse-indication information can be performed by only a person in charge given a higher privilege than that of common operators.

Next, a characteristic compound identification process performed in the LC-MS system in the present embodiment with nonuse-indication information set in the compound database 33 as previously described is described with reference to 2A, FIG. 29, and FIG. 2C.

On a chromatogram created based on data collected through measurement performed on a target sample and displayed on the screen of the display unit 5, an operator specifies a peak estimated to originate from a compound intended to be identified, using the input unit 4. Then, data obtained at a time point of the peak top of the specified peak is read from the measurement data storage section 31, and the mass spectrum creating section 32 creates a mass spectrum based on this data and transmits the mass spectrum to the database search processing section 34. The database search processing section 34 searches the compound database 33 for a compound the spectral pattern of which is similar to this given mass spectrum (hereafter, referred to as a target mass spectrum), so as to identify an unknown compound intended.

The database search in the database search processing section 34 is performed in two steps: (I) rough extraction of compound candidates having similar spectral patterns, performed by the compound candidate extracting section 342, and (II) calculation of a score indicating similarity of spectral pattern in detail for each of the compound candidates, performed by the scoring section 343. Based on the calculated score, narrowing and ranking final candidates are performed by the candidate ranking section 344. The first nonuse-indication information previously described is referred to in both of the steps (I) and (II), and the second nonuse-indication information previously described is referred to in only the step (H).

In extracting the compounds having spectral patterns similar to the spectral pattern of the target mass spectrum, the compound candidate extracting section 342 reads mass spectrum data 332 corresponding to compounds registered in the compound database 33 one by one. At this point, the compound candidate extracting section 342 also reads the first nonuse-indication information stored in the form of the attribute information 333. The unnecessary information deleting section 341 deletes a peak to which first nonuse-indication information is set in the mass spectrum data, and the compound candidate extracting section 342 assesses whether or not the mass spectrum subjected to the peak deleting process is similar to the target mass spectrum in spectral pattern.

Now, assume that, of peaks on a mass spectrum illustrated in FIG. 2A collected in the compound database 33, flags of first nonuse-indication information are set to peaks attached with the mark "O", and flags of second nonuse-indication information are set to peaks attached with the mark "Δ". In this case, in the compound candidate extraction, the unnecessary information deleting section 341 deletes the peaks set with first nonuse-indication information, and thus the mass spectrum to be transmitted to the compound candidate extracting section 342 for the assessment of spectral pattern similarity becomes such as a mass spectrum illustrated in FIG. 2B. That is, the peaks set with the mark "O" in FIG. 2A are ignored in the assessment of spectral pattern similarity. Therefore, setting first nonuse-indication information to noise peaks accidentally appearing in actual measurement for the registration in the database enables compound candidate extraction being the same as in the case of using a mass spectrum in which such noise peaks are substantially absent.

A specific algorithm for the compound candidate extraction does not matter in particular, but the assessment of similarity may be performed in such a manner as to focus only on a mass-to-charge-ratio position at which a peak appears irrespective of the magnitude of the signal intensity of the peak as long as the signal intensity is not less than a predetermined threshold value, so as to search out compounds from the compound database 33 registering a huge number of compounds in a time as short as possible.

Next, for each of the plurality of extracted compound candidates, the scoring section 343 calculates a score obtained by quantifying the degree of similarity in spectral pattern between the target mass spectrum and a mass spectrum corresponding to the compound candidate. In this calculation of the score, both first nonuse-indication information and second nonuse-indication information stored in the compound database 33 are read as attribute information 333, and the unnecessary information deleting section 341 deletes, from read mass spectrum data, a peak with at least one of the first nonuse-indication information and the second nonuse-indication information set. Then, the scoring section 343 calculates a score based on, for example, differences in positions and signal intensities of peaks between the mass spectrum subjected to the peak deleting process and the target mass spectrum.

In the example illustrated in FIG. 2A, FIG. 2B, and FIG. 2C, since the unnecessary information deleting section 341 deletes, in scoring, the peak with at least one of the first nonuse-indication information and the second nonuse-indication information set, the mass spectrum to the transmitted to the scoring section 343 becomes such as a mass spectrum illustrated in FIG. 2C. That is, both of the peaks set with the mark "O" and the peaks set with the mark "Δ", in FIG. 2A, are ignored in scoring. Therefore, setting second nonuse-indication information to, for example, an ion peak originating from a main skeleton not useful for discriminating from similar compounds prevents the similarity of such a peak from being reflected on the score and makes the similarity and the dissimilarity of another peak originating from a specific partial structure clearly appear in the score. As a result, the score of a compound candidate having a specific partial structure identical to the specific partial structure of the target compound is increased. In addition, setting first nonuse-indication information to a noise peak or the like as previously described prevents the noise peak from being reflected on the score, improving the accuracy of the score.

After calculating the score for each of the plurality of compound candidates, the candidate ranking section 344 exclude, if any, a compound candidate having an extremely low score from a list. Then, the candidate ranking section 344 sorts the remaining compound candidates in a descending order of scores, and displays the compound candidates on the screen of the display unit 5 together with their scores, as an identification result. As seen from the above, the LC-MS system in the present embodiment allows nonuse-indication information to be set to any peak on a mass spectrum registered in the compound database 33 and in searching the database, ignores some peaks using this nonuse-indication information to search for more likely compound candidates, so as to rank the compound candidates in terms of likelihood with high accuracy.

Figure 3:
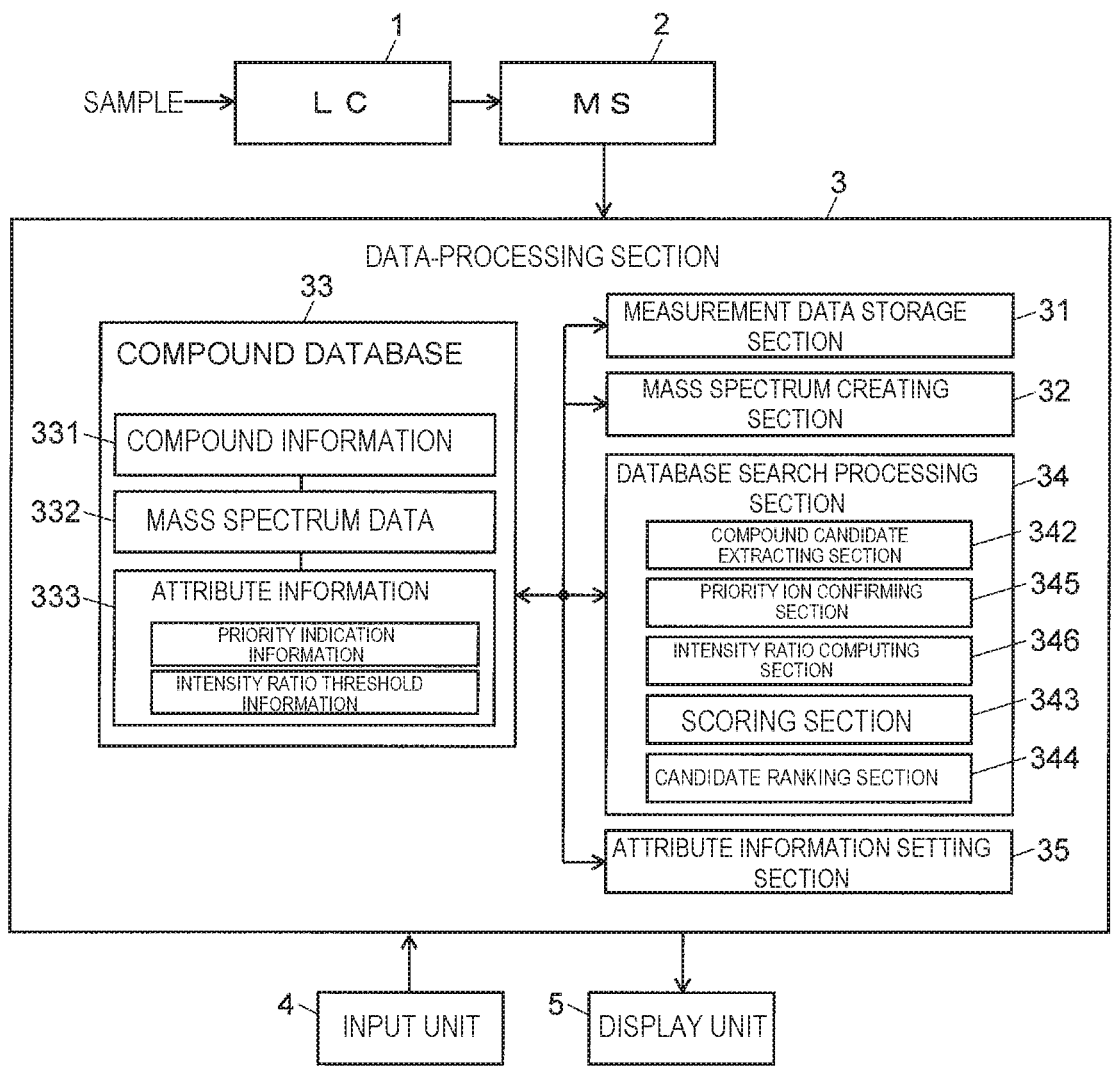
FIG. 3 is a schematic configuration diagram of a second embodiment of an LC-MS system including a mass spectrometry data-processing system according to the present invention.
Figure 4:
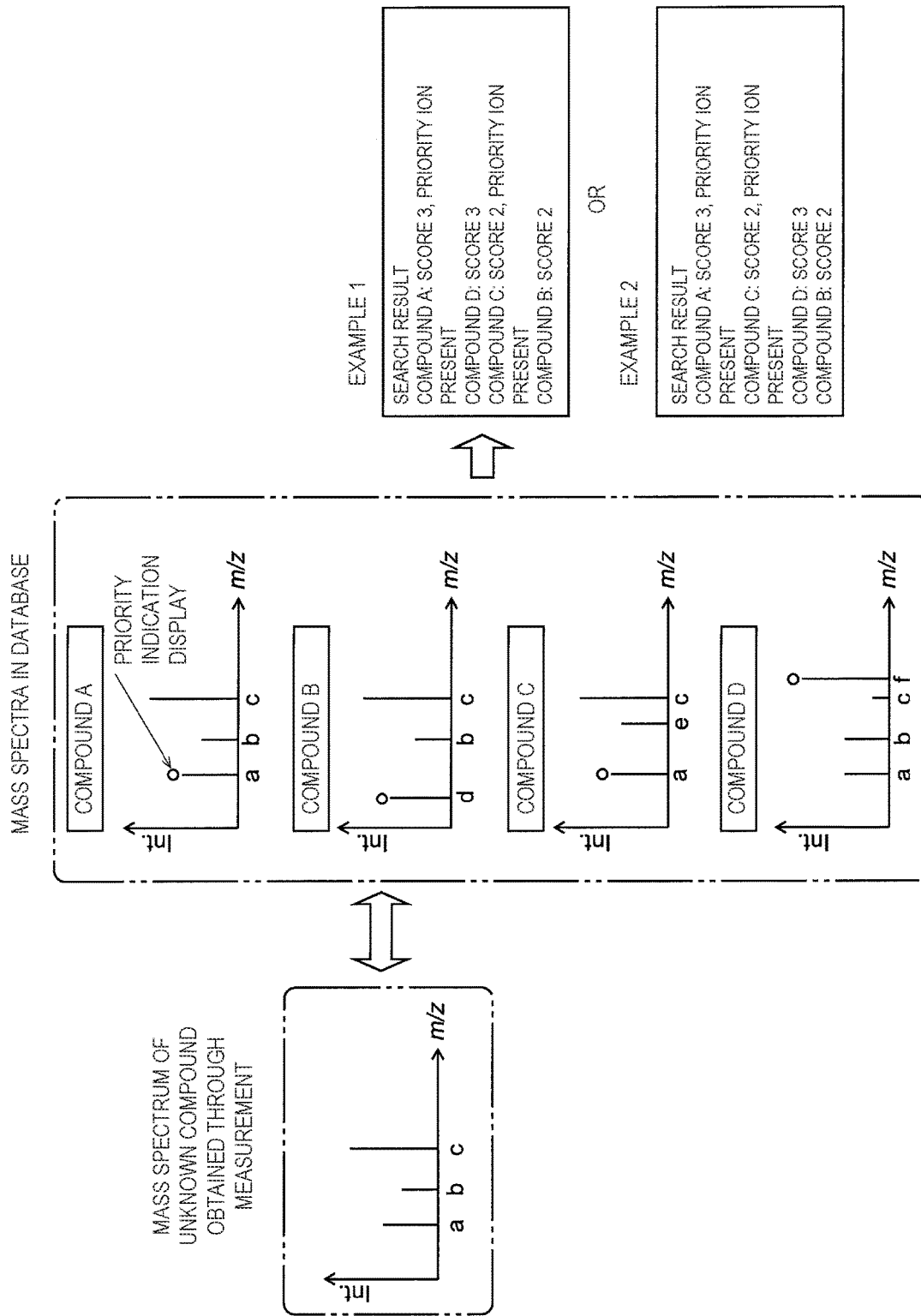
FIG. 4 is a diagram illustrating an example of a compound identification process in the LC-MS system in the second embodiment.

Next, a second embodiment of the LC-MS system using the mass spectrometry data-processing system according to the present invention is described with reference to the attached drawings. FIG. 3 is a schematic configuration diagram of the LC-MS system in this second embodiment, and FIG. 4 is a diagram illustrating an example of a compound identification process in the LC-MS system in the second embodiment. In FIG. 3, components identical to those of the configuration illustrated in FIG. 1 are denoted by the same reference numerals.

In this LC-MS system, attribute information 333 corresponding to mass spectrum data 332 stored in the compound database 33 includes priority indication information and intensity ratio threshold information. In addition, the database search processing section 34 includes a priority ion confirming section 345 and an intensity ratio computing section 346.

The priority indication information can be set, as with the nonuse-indication information in the first embodiment, by a user as appropriate for mass spectrum data 332 on any compound having already been registered in the compound database 33, or for mass spectrum data 332 on any compound to be newly registered in the compound database 33. Meanwhile, the intensity ratio threshold information is numerical value information that can be set, by a user as appropriate, to a peak on a mass spectrum set with priority indication information. This intensity ratio threshold information is for indicating a threshold for the assessment of a relative signal intensity of a peak intended (i.e., set with the priority indication information) to a predetermined reference intensity, which is described later. Specifically, for example, the reference intensity may be determined in the form of the signal intensity of a peak at a specified mass-to-charge ratio on the mass spectrum or a maximum intensity observed on the mass spectrum.

Next, a characteristic compound identification process performed in the LC-MS system in the present embodiment with priority indication information and intensity ratio threshold information set in the compound database 33 as previously described is described with reference to FIG. 4.

As in the first embodiment, an operator specifies, on a chromatogram, a peak estimated to originate from a compound intended to be identified, using the input unit 4. Then, the database search processing section 34 searches the compound database 33 for a compound similar in target mass spectrum in spectral pattern. In this database search, the compound candidate extracting section 342 performs the rough extraction of compound candidates having similar spectral patterns, and subsequently, the scoring section 343 performs the calculation of a score indicating similarity of spectral pattern in detail for each of the compound candidates. Here, unlike the first embodiment, no nonuse-indication information is set as attribute information, and thus all peaks in mass spectrum data 332 registered in the compound database 33 are used in the database search.

It is assumed here, for ease of description, that the scoring section 343 performs the scoring based only on the degree of match between the mass-to-charge ratio of a peak on the target mass spectrum and the mass-to-charge ratio of a peak on the mass spectrum of each compound candidate, and the similarity between the peaks in signal intensity is ignored. As illustrated in FIG. 4, it is assumed that peaks are observed at three mass-to-charge ratios, m/z=a, b, and c, in the target mass spectrum. On the mass spectrum of each compound candidate, the scoring section 343 checks whether or not peaks are present at the three mass-to-charge ratios (actually, within mass-to-charge-ratio ranges having predetermined margins across the mass-to-charge ratios) and increments a score by one whenever a peak is present at the same mass-to-charge ratio as one of the three mass-to-charge ratios. Now, when the mass spectra of four compound candidates A, B, C, and D are such as those illustrated in FIG. 4, the calculation of scores based on matches between the mass-to-charge ratios of peaks yields a score of three for the compounds A and D because the number of peaks of matched mass-to-charge ratios is three, and a score of two for the compounds B and C because the number of peaks of matched mass-to-charge ratios is two.

In parallel to or following this process, the priority ion confirming section 345 checks whether or not priority indication information is set to a peak for which a score is incremented. Then, when priority indication information is set to a peak for which a score is incremented, the compound candidate is attached with a flag indicating the fact. In the example illustrated in FIG. 4, there are two compounds A and C having priority indication information set to a peak for which a score is incremented. Thus, the two compound candidates are each attached with the flag. The candidate ranking section 344 excludes, if any, a compound candidate having an extremely low score from the list, sorts the remaining compound candidates in a descending order of scores, and displays the compound candidates on the screen of the display unit 5 together with their scores, as an identification result. At this point, a display indicating that a priority ion is contained is performed together on a compound candidate attached with a flag. In EXAMPLE 1 in FIG. 4, the text information indicating "PRIORITY ION PRESENT" is displayed, but the specific form of displaying is not limited to this.

In addition, there are cases where the presence/absence of a priority ion matters more when the difference between scores is small, and thus as illustrated in EXAMPLE 2 in FIG. 4, a compound containing a priority ion may be arranged at a higher rank even when the compound has a low score.

As seen from the above, in the result of the database search, a compound containing an ion set with priority indication information is discriminable from compounds not containing such an ion, and is displayed in some cases preferentially, that is, in a higher rank of a list, even having a low score. For this reason, for example, in the case where an ion characteristic of an intended compound or an ion useful for distinguishing the compound from the other compounds is known, setting priority indication information to such ions allows an operator to easily select a correct compound candidate from a search result.

In addition, in the case where intensity ratio threshold information is set together with priority indication information when the priority ion confirming section 345 attaches a flag indicating the presence of priority indication information to a compound candidate in accordance with the presence/absence of the setting of the priority indication information, the intensity ratio computing section 346 can perform the following process. That is, the intensity ratio computing section 346 determines, on the mass spectrum of the compound candidate, the signal intensity value of a peak considered to be an intensity reference of a relative intensity ratio and the signal intensity value of a peak set with priority indication information, to calculate an intensity ratio. Then, the intensity ratio is compared with a threshold indicated by the intensity ratio threshold information, and if the intensity ratio is equal to or greater than the threshold, the priority indication information is assessed to be effective. Then, a flag is attached to a compound candidate containing only an ion set with the priority indication information assessed to be effective. This allows a display indicating that a compound candidate contains a priority ion to be performed in a search result only when the compound candidate contains an ion set with the priority indication information, and at the same time when the signal intensity of the ion reaches a reliable degree. In addition, it is allowed to perform a display indicating that a priority ion is contained irrespective of the result of assessing the intensity ratio, and moreover, to perform a display indicating the result of assessing whether the intensity ratio is equal to or greater than the threshold indicated by the intensity ratio threshold information.

As is clear from the previous description, the nonuse-indication information used in the LC-MS system in the first embodiment can be used concurrently with the priority indication information used in the LC-MS system in the second embodiment. That is, it may suffice to perform a database search excluding an ion peak set with nonuse-indication information to extract compound candidates, then assess whether or not an ion peak set with priority indication information is contained, and make the result of the assessment being reflected in the display of search result. This allows the exclusion of compounds other than a target compound and having a structure similar to the structure of the target compound, from a search result, and further, an explicit indication of compound candidates having a partial structure characteristic of the target compound, in the search result.

It should be noted that the previously-described embodiments are an application of the present invention to an LC-MS, and the present invention is applicable to general mass spectrometers performing compound identification using mass spectra registered in a compound database such as an LC-MS/MS, a GC-MS, a GC-MS/MS, as well as a stand-alone mass spectrometer not in combination with an LC or a GC.

It should be noted that the previously-described embodiments are a mere example of the present invention, and any change, modification or addition appropriately made within the scope consistent with the present invention will evidently fall within the scope of claims of the present patent application.

REFERENCE SIGNS LIST

1 . . . Chromatograph
2 . . . Mass Spectrometry Section
3 . . . Data-Processing Section
31 . . . Measurement Data Storage Section
32 . . . Mass Spectrum Creating Section
33 . . . Compound Database
331 . . . Compound Information
332 . . . Mass Spectrum Data
333 . . . Attribute Information
34 . . . Database Search Processing Section
341 . . . Unnecessary information Deleting Section
342 . . . Compound Candidate Extracting Section
343 . . . Scoring Section
344 . . . Candidate Ranking Section
345 . . . Priority ion Confirming Section
346 . . . Intensity Ratio Computing Section
35 . . . Attribute Information Setting Section

The invention claimed is:

1. A mass spectrometry system, comprising:
a mass analyzer configured to separate a sample including an unknown compound into compounds and configured to obtain a mass spectrum of the unknown compound;
a data-processing system including:
 a) a database in which mass spectra of known compounds are collected;
 b) an input unit configured to allow a user to set nonuse-indication information indicating that an ion peak is not used in a database search; and
 c) a search processor configured to perform the database search using the mass spectrum of the unknown compound and configured to output at least one identification result resulting from the database search; and
a display configured to display the at least one identification result, wherein
the data-processing system is configured to (i) set the nonuse-indication information to an ion peak of one of the mass spectra of known compounds collected in the database, (ii) estimate the unknown compound through a use of the one of the mass spectra of known compounds from which the ion peak set with the nonuse-indication information is excluded, and (iii) store the nonuse-indication information in the database.

2. The mass spectrometry system according to claim 1, wherein
the search processor includes: a candidate extracting section configured to compare patterns of mass spectra to extract a plurality of compounds to be candidates; and a ranking section configured to rank the plurality of extracted candidates based on the similarities of mass spectra,
the nonuse-indication information includes: first nonuse-indication information indicating that an ion peak attached with the first nonuse-indication information is not used in both of extracting the compounds by the candidate extracting section and ranking the compound candidates by the ranking section; and second nonuse-indication information indicating that an ion peak attached with the second nonuse-indication information is not used only in ranking the compound candidates by the ranking section,
the candidate extracting section extracts a plurality of compound candidates using mass spectra from which the peak attached with the first nonuse-indication information is excluded, and the ranking section ranks compound candidates using mass spectrum from which the ion peak attached with at least one of the first nonuse-indication information and the second nonuse-indication information is excluded, and
the display displays at least one of the plurality of compound candidates that are ranked by the ranking section, as the at least one identification result, and displays a ranking or score provided by the ranking section for each of the at least one identification result.

3. A mass spectrometry system, comprising:
a mass analyzer configured to separate a sample including an unknown compound into compounds and configured to obtain a mass spectrum of the unknown compound, and
a data-processing system including:
 a) a database in which mass spectra of known compounds are collected;
 b) an input unit configured to allow a user to set priority indication information indicating that an ion peak is used preferentially in a database search;
 c) a search processor configured to perform the database search using the mass spectrum of the unknown compound and configured to output compound candidates resulting from the database search; and
a display configured to display the compound candidates, wherein
the data-processing system is configured to (i) set the priority indication information to an ion peak of one of the mass spectra of known compounds collected in the database, (ii) estimate the unknown compound by comparing the mass spectrum of the unknown compound with the one of the mass spectra of known compounds, (iii) extract the compound candidates that are supposed to be an unknown compound of interest, (iv) extract the compound candidates on one of conditions that the ion peak set with the priority indication information is present on the mass spectrum of the unknown compound or create a search result that allows, of compound candidates extracted through a database search not using the priority indication information, a compound candidate of which an ion peak set with the priority indication information is present on the mass spectrum of the unknown compound to be distinguished from other compound candidates, and (v) store the priority indication information in the database.

4. The mass spectrometry system according to claim 3, wherein the database is configured to allow threshold information to be set to an ion peak set with the priority indication information in addition to the priority indication information, the threshold information being used for assessing an intensity ratio of a signal intensity of the ion peak to a signal intensity of a specific peak on a mass spectrum in which the ion peak is present.

5. The mass spectrometry system according to claim 4, wherein the search processor is configured to extract compound candidates on one of conditions that an ion peak set with the priority indication information is present on the mass spectrum of the unknown compound, and, on the mass spectrum of the unknown compound, the intensity ratio of the signal intensity of the ion peak to the signal intensity of the specific peak is equal to or greater than the threshold information set to the ion peak together with the priority indication information.

6. The mass spectrometry system according to claim 1, wherein the nonuse-indication information includes at least one flag.

7. The mass spectrometry system according to claim 3, wherein the priority indication information includes at least one flag.

\* \* \* \* \*